(12) United States Patent
Chen

(10) Patent No.: US 9,547,063 B2
(45) Date of Patent: Jan. 17, 2017

(54) CALCULATING SPECIFIC ABSORPTION RATE (SAR) WITH MAGNETIC RESONANCE SIGNALS

(71) Applicant: TOSHIBA MEDICAL SYSTEMS CORPORATION, Tochigi (JP)

(72) Inventor: Xin Chen, Beachwood, OH (US)

(73) Assignee: TOSHIBA MEDICAL SYSTEMS CORPORATION, Otawara-shi, Tochigi-ken (JP)

( * ) Notice: Subject to any disclaimer, the term of this patent is extended or adjusted under 35 U.S.C. 154(b) by 461 days.

(21) Appl. No.: 14/171,026

(22) Filed: Feb. 3, 2014

(65) Prior Publication Data

US 2015/0219738 A1 Aug. 6, 2015

(51) Int. Cl.
  G01V 3/00 (2006.01)
  G01R 33/58 (2006.01)
  A61B 5/055 (2006.01)
  G01R 33/28 (2006.01)

(52) U.S. Cl.
  CPC ............... *G01R 33/58* (2013.01); *A61B 5/055* (2013.01); *G01R 33/288* (2013.01)

(58) Field of Classification Search
  CPC ........ G01R 33/288; G01R 33/88; A61B 5/055
  USPC ......................................................... 324/308
  See application file for complete search history.

(56) References Cited

U.S. PATENT DOCUMENTS

| | | | | |
|---|---|---|---|---|
| 8,717,021 B2* | 5/2014 | Bottomley | ........... | G01R 33/288 324/309 |
| 2011/0263969 A1* | 10/2011 | Fontius | ................ | G01R 33/288 600/412 |
| 2012/0086449 A1 | 4/2012 | Graesslin et al. | | |
| 2012/0226137 A1* | 9/2012 | Ito | ........................ | G01R 33/288 600/410 |
| 2015/0185298 A1* | 7/2015 | Crozier | .................. | G01R 33/58 702/19 |

OTHER PUBLICATIONS

U.S. Appl. No. 13/739,236, filed Jan. 11, 2013, Hamamura, et al.
NEMA Standards Publication MS 8-2008, Charaxterization of the Specific Absorption Rate for Magnetic Resonance Imaging Systems, pp. 1-15, published by National Electrical Manufacturers Association, Rossyln, VA (2008).
El-Sharkawy, et al., "A multichannel, real-time MRI RF power monitor for independent SAR determination," *Med. Phys.*, vol. 39, No. 5, pp. 2334-2341 (May 2012).
Graesslin, et al., "Real-time SAR Monitoring to ensure Patient Safety for Parallel Transmission Systems," *Proc. Intl. Soc. Mag. Reson. Med.*, vol. 15, p. 1086 (2007).
Graesslin, et al., "Real-time Global and Local SAR Monitoring for Parallel Transmission Systems," *Proc. Intl. Soc. Mag. Reson, Med.*, vol. 17, p. 302 (2009).

(Continued)

*Primary Examiner* — Susan Lee
(74) *Attorney, Agent, or Firm* — Nixon & Vanderhye P.C.

(57) ABSTRACT

A magnetic resonance imaging (MRI) system, MRI method and a computer readable medium are configured to determine a specific absorption rate (SAR) for the patient based on at least (a) NMR signal strength at a phantom when the at least one RF coil is loaded with the patient for an MRI scan, and (b) NMR signal strength at the phantom when the at least one RF coil is not loaded with the patient for an MRI scan.

20 Claims, 6 Drawing Sheets

(56) References Cited

OTHER PUBLICATIONS

Graesslin, "Parallel Transmission: A Comprehensive RF Safety Concept," *PIERS Proceedings*, Cambridge, USA, pp. 698-700 (Jul. 2-6, 2008).
Carlson et al., "Rapid Radiofrequency Calibration in MRI", Magnetic Resonance in Medicine 15, (1990); pp. 438-445.

* cited by examiner

CALCULATING SPECIFIC ABSORPTION RATE (SAR) WITH MAGNETIC RESONANCE SIGNALS

TECHNICAL FIELD

The subject matter below relates generally to magnetic resonance imaging (MRI) apparatus and process. In particular, the MRI apparatus and method described below involve the determination of specific absorption rate (SAR) using magnetic resonance (MR) signals.

DETAILED DESCRIPTION

Figure 1:
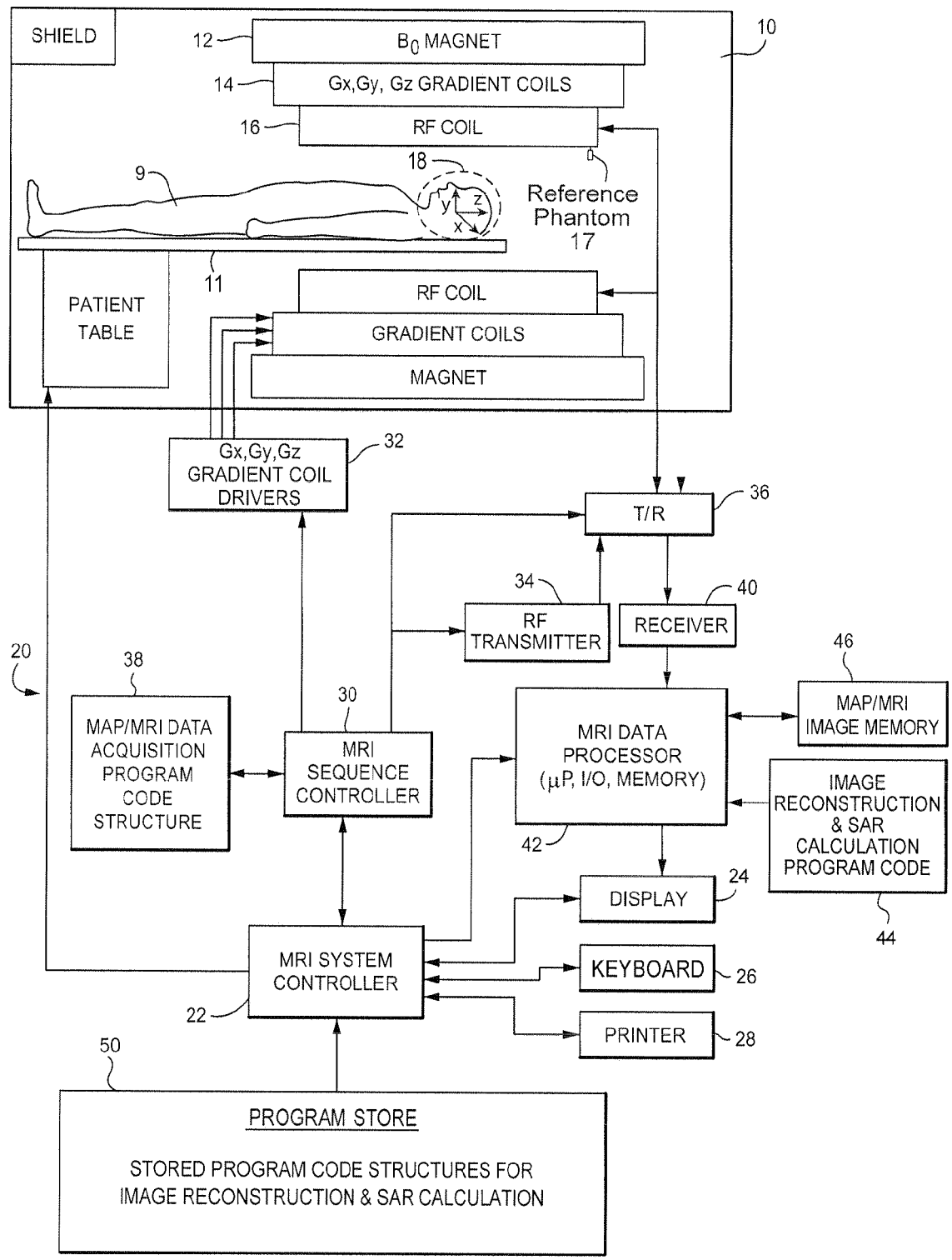
FIG. 1 is a high-level schematic block diagram of an exemplary MRI system embodiment configured to more accurately determine SAR using MR signals.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field Bo magnet 12, a Gx, Gy and Gz gradient coil set 14 and an RF coil assembly 16. Along the horizontal axis of this cylindrical array of elements is an imaging volume 18 shown as substantially encompassing the anatomy of interest (i.e., region of interest or "ROI") for a patient 9 (e.g., the head) supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as RF transmitter 34 and transmit/receive switch 36 (if the same RF coil is used for both transmission and reception). As those skilled in the art will appreciate, many different types of RF coils (e.g., whole body coils, surface coils, birdcage coils, coil arrays, etc.) may be employed to transmit and/or receive RF signals to/from the ROI in the imaging volume. The MRI sequence controller 30 also has access to suitable program code structure 38 for implementing MRI data acquisition sequences already available in the repertoire of the MRI sequence controller 30.

The MRI system 20 includes an RF receiver 40 providing input to data processor 42 so as to create processed image data which may be sent to display 24 (or elsewhere, e.g., to storage for later viewing). The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures for determining a specific absorption rate (SAR) for a patient based on MR signals, a related graphical user interface (GUI), operator inputs to same, etc. are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

A pulse energy method as described in NEMA (National Electrical Manufacturers Association) Standards Publication MS 8-2008 is commonly used for calculating SAR (Specific Absorption Rate) in MRI. As will be understood, there are prescribed health and safety standards that limit the SAR so as to prevent patient damage during MRI. The NEMA standard calculates power absorbed by a patient by subtracting the RF power absorbed by the scanner ($P_{coil}$) from the total RF power (P) transmitted by the RF coil, the difference being divided by the patient's weight.

$$SAR = \frac{1}{\text{weight}}(P - P_{coil}) \quad \text{[Equation 1]}$$

NEMA MS 8-2008 specifies $P_{coil}$ to be measured as the transmitted RF power required when the scanner is unloaded (i.e., no patient is present). The underlying assumption is that the power absorbed by the scanner when a patient is later loaded into it (i.e., the real definition of $P_{coil}$) is equal to the RF power absorbed when the scanner is not loaded (i.e., the measured power). In other words, it is assumed that between actual patient-loaded imaging and earlier unloaded calibration measurements, the required B1 RF field is the same and thus the same current will flow in the transmit coil and the same power is consumed in the scanner.

One solution is to measure actual RF current passing along the transmit coil conductor and then to correct the SAR calculation (since the transmit coil is the dominant source of RF power absorption in the MRI scanner). The revised SAR calculation equation is:

$$SAR = \frac{1}{\text{Weight}}\left\{P_{scan} - P_{unloaded} \cdot \left(\frac{I_{scan}}{I_{unloaded}}\right)^2\right\} \quad \text{[Equation 2]}$$

SAR (Specific Absorption Rate) is defined as the energy absorbed by patient tissue per second per kg, which is an important parameter in MRI for patient safety. It is calculated based on the power absorbed by a patient divided by the patient's weight:

$$SAR = \frac{P_{patient}}{\text{weight}} (w/kg) \quad \text{[Equation 3]}$$

The RF power going into the patient tissue is calculated by subtracting (a) the RF power absorbed by the scanner from (b) the total incident RF power:

$$P_{patient} = P_{total} - P_{coil} \quad \text{[Equation 4]}$$

The conventional method of measuring the power $P_{coil}$ absorbed by the scanner is to assume it is equivalent to the power absorbed by the unloaded coil (e.g., since the scanner adjusts the NMR nutation flip angle to have the same B1 RF field). This assumes the same current flows in the transmit coil and the same RF power is consumed in the coil—despite variations in patient size, weight, imaging landmark, etc.:

$$SAR = \frac{1}{\text{weight}}(P_{scan} - P_{unloaded}) \quad \text{[Equation 5]}$$

However, this assumption is not accurate in a high RF frequency (e.g., high field MRI) case as the scattered RF field caused by the patient body (e.g., due to eddy currents and dielectric effects) becomes dominant.

However, non-uniform distribution of B1 RF fields always exists in MRI. At lower Bo field strengths (and therefore lower Larmor frequencies), it may be considered trivial for some purposes. But in a 3T (3 Tesla) or higher magnetic field, the resulting higher Larmor frequencies (and lower wavelengths) cause more eddy currents and dielectric effects in the human body. This results in an even more non-uniform distribution of B1 RF fields.

In short, the assumption embedded in the NEMA pulse energy method is not true—especially at high frequencies. Table 1 below shows $P_{coil}$ is not the same between different imaging samples (simulation result). This causes errors in a traditional SAR calculation that degrades imaging performance or makes an unsafe patient environment.

TABLE 1

| Phantom | Power (w) | $P_{coil}$ (w) |
|---|---|---|
| 30 L saline | 15190 | 9903 |
| 2.5 L $CuSO_4$ | 3361 | 3184 |
| 2.7 L mineral oil | 6467 | 6467 |

A proper definition for $P_{coil}$ is the actual RF power absorbed by the scanner. A cause of the problem noted above is using the unloaded power as something equal to $P_{coil}$, which is not accurate in a high field MRI situation.

The measurement of power absorbed in the scanner should be modified. If RF coil current when a patient is loaded into the coil could be measured, then $P_{coil}$ could be calculated by:

$$P_{coil} = I^2_{scan} \cdot R_{coil} \quad \text{[Equation 6]}$$

where $I_{scan}$ is the current in the coil when a patient is loaded therein, and $R_{coil}$ is the resistance of the transmit coil.

When the scanner is unloaded, the equation becomes:

$$P_{unloaded} = I^2_{unloaded} \cdot R_{coil}$$

since the coil resistance does not change, substituting the second equation into the first becomes:

$$P_{coil} = \left\{\left(\frac{I_{scan}}{I_{unloaded}}\right)^2\right\} \cdot P_{unloaded} \quad \text{[Equation 7]}$$

Therefore, SAR can be calculated as:

$$SAR = \frac{1}{\text{weight}}\left\{P_{scan} - P_{unloaded} \cdot \left(\frac{I_{scan}}{I_{unloaded}}\right)^2\right\} \quad \text{[Equation 8]}$$

This can then provide a SAR measurement even when B1 and current on the coil are not constant and/or are unknown.

To thus calculate SAR, the current ratio ($I_{scan} \div I_{unloaded}$) has to be measured.

Prior related copending application Ser. No. 13/739,236 filed Jan. 11, 2013, proposes a solution which utilizes at least one small pickup loop within the RF coil. However, exposing the pickup loop induces unnecessary voltage in the loop which may introduce measurement error. Implementing such pickup loops also increase product complexity and cost.

Another major disadvantage of introducing a pick up loop is that the loop itself and the cables transmitting signals from the loop to external computers can interfere with the B1 field produced by the RF coil, which may disturb the normal functioning of the RF coils and the scan. To "decouple" the pick-up loop and its associated hardware components from the existing RF coil and associated components requires additional engineering considerations, time, and cost.

Figure 2:
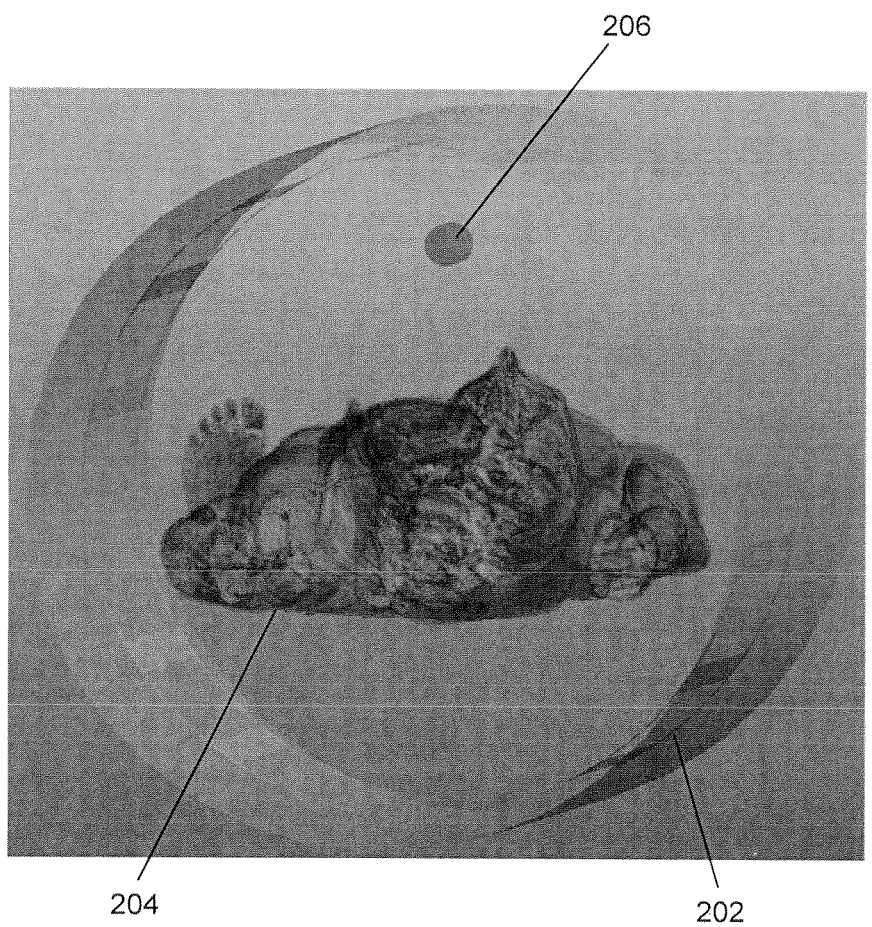
FIG. 2 illustrates a patient loaded into a radio frequency (RF) coil for scanning in an MRI system, and a reference phantom located inside the RF coil, in accordance with one or more embodiments.

In the present approach to measuring SAR, as depicted in FIG. 1, a small non-loading reference phantom 17 (e.g., a small bottle of oil) is placed in close proximity to the transmit coil element(s) 16 (e.g., a birdcage body coil as depicted in FIG. 2) and at a distance from the patient such that it is within the local RF magnetic field ($B_1$) and field of view of the RF coil, but is not substantially affected by the scattered magnetic field created by the patient body.

The RF magnetic field $B_1$ is circularly polarized to excite nucleus spins. The $B_1$ field component which has polarization consistent with spin precession is often called $B_1^+$ (transmit field), while the opposite polarization is $B_1^-$ (receive field). Only $B_1^+$ can be measured based on image intensities. Since the $B_1^-$ component does not contribute to generating MR signals, it cannot be measured from images.

For an unloaded quadrature drive (QD) birdcage coil, $B_1^+=B_1$, and $B_1^-=0$. $B_1^+$ is the only field produced by the current source $I_{unloaded}$. Therefore, $$B_{1\_unloaded}^+ = cI_{unloaded} \quad \text{[Equation 9]}$$

where c is a constant determined solely by the coil structure and dimensions.

When an imaging subject (e.g., patient, human body) is present in the coil, the perfect circular polarization will be disturbed, and both $B_1^+$ and $B_1^-$ components exist in the subject. However, at a spatial location that is close to coil rung but far away from the imaging subject, the original $B_1^+$ field is less disturbed. The $B_1^+$ field measured at this point is closely related to the coil current:

$$B_{1\_scan,out}^+ = cI_{scan} \quad \text{[Equation 10]}$$

where c is a constant (same constant used in equation 9).

Figure 3:
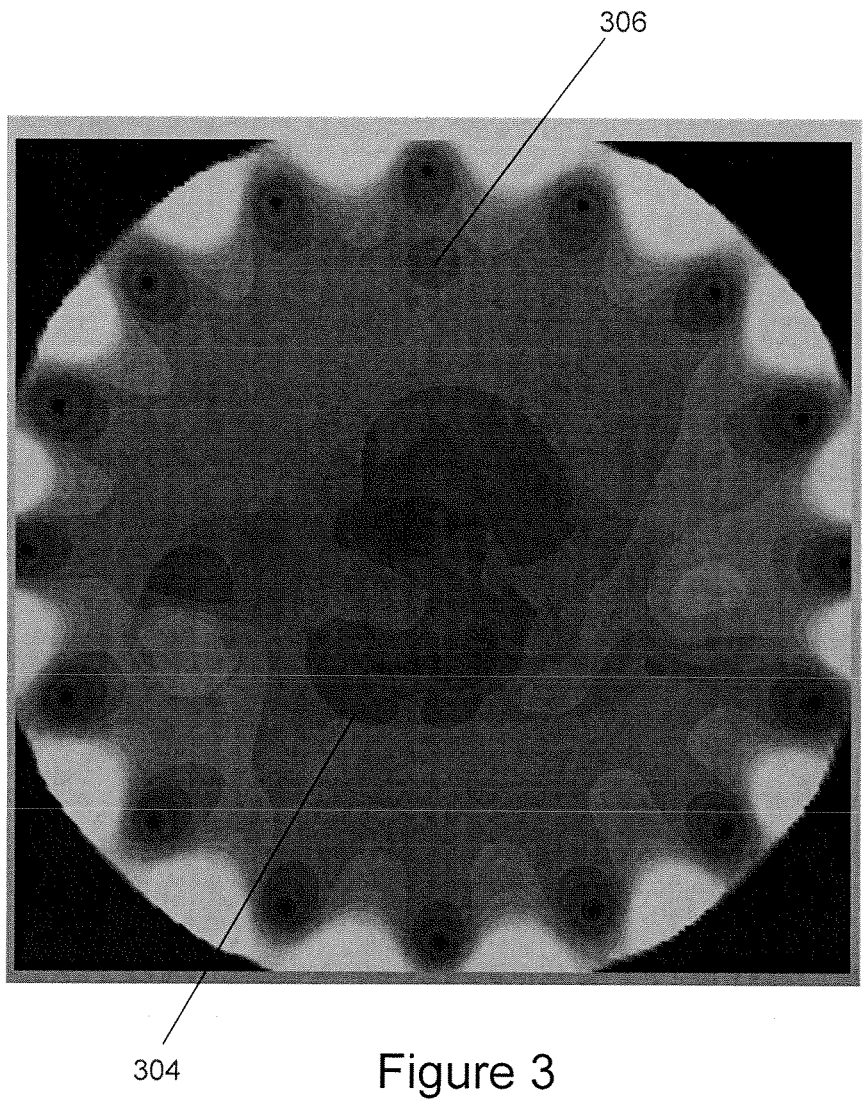
FIG. 3 depicts a simulation result of the magnetic field in a RF coil, such as the RF coil of FIG. 2 with the patient loaded and with the reference phantom in accordance with one or more embodiments.

FIG. 2 shows a human subject 204 (e.g. patient) loaded into a birdcage body coil 202. A small reference phantom 206 is placed in the bore close to coil elements. Simulation showed, as illustrated in FIG. 3, that although $B_1^+$ field is significantly disturbed in the human subject's body (see scattered field 304), it remained mostly undisturbed close to coil elements (e.g., coil surface, such as where the reference phantom 17 is located 306). Therefore, $B_1^+$ field is closely related to current flow on the coil elements (i.e., impact from scattered fields is small at this spatial location 306).

Therefore, $B_1^+$ field measurements in the small reference phantom with unloaded and loaded conditions (i.e., when the patient is not loaded and loaded in the RF coil for a MRI scan) can yield the current ratio of interest:

$$\frac{B_{1\_scan,out}^+}{B_{1\_unloaded}^+} = \frac{I_{scan}}{I_{unloaded}} \quad \text{[Equation 11]}$$

In embodiments, the ratio of $B_1^+$ field, is determined efficiently with a field echo (FE) sequence with a small flip angle (e.g., flip angle less than 30°). The image signal of such a sequence is given by $$\text{Signal} = a \cdot PD \cdot \sin(\gamma B_1^+ \tau) \cdot |B_1^-| \approx a \cdot PD \cdot |\gamma B_1^+ \tau| \cdot |B_1^-| \quad \text{[Equation 12]}$$

where a is a constant determined by hardware setting (e.g., receiver gain), and PD is proton density. If such a sequence is executed with and without the imaging subject being loaded, with all hardware settings remaining unchanged, the image signal strength only depends on $B_1^+$ strength. Measuring image signal with the small reference phantom will yield $$\frac{signal_{scan}}{signal_{unloaded}} = \frac{B_{1\_scan}^+}{B_{1\_unloaded}^+} \quad \text{[Equation 13]}$$
$$= \frac{I_{scan}}{I_{unloaded}}$$

Therefore, SAR can be calculated as $$SAR = \frac{1}{\text{Weight}}\left\{P_{scan} - P_{unloaded} \cdot \left(\frac{I_{scan}}{I_{unloaded}}\right)^2\right\} \quad \text{[Equation 14]}$$
$$= \frac{1}{\text{Weight}}\left\{P_{scan} - P_{unloaded} \cdot \left(\frac{signal_{scan}}{signal_{unloaded}}\right)^2\right\}$$

with the image signal measured within a small non-loading reference phantom located in the proximity of coil rungs and far away from the imaging subject.

The strength of the image signal at the reference phantom when the RF coil is unloaded can be determined by determining signal intensity in the corresponding MRI image at a selected point or slice within the area of the reference phantom. The strength of the image signal at the reference phantom when the RF coil is loaded can be determined similarly by determining signal intensity in the corresponding MRI image at a selected point or slice within the area of the reference phantom while the RF coil is loaded. Identifying the reference phantom in the MRI images may be done manually or automatically.

Such sequence may be used as part of routine clinical imaging protocol, such as a locator scan, and does not require additional scan time, data processing or hardware change (except, of course, for provision of the reference phantom structure).

To avoid interference on the clinical image, the reference phantom may be placed far from the magnetic center in longitudinal (Z) direction, and/or be filled with chemicals having protons different from water protons so that it is "off-resonance" from water proton resonance frequency. When collecting the signal from the reference phantom, dedicated RF pulses at one or more specific reference phantom frequencies will be applied. When imaging is performed afterwards at water proton resonance frequency, no reference phantom signal will be collected.

Since current flow may not be constant over the entire birdcage coil, multiple reference phantoms may be placed at different locations in the bore of the RF coil to improve measurement accuracy.

Figure 4:
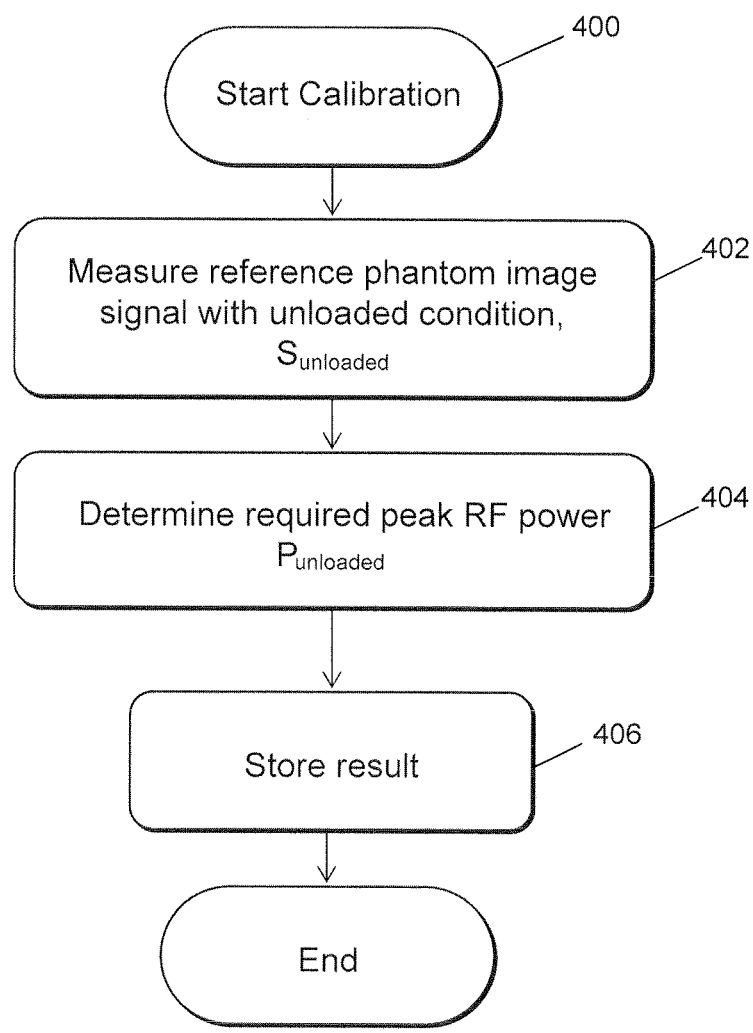
FIG. 4 is a flowchart of a calibration process to determine power and signal parameters when a patient is not loaded in a RF coil in accordance with one or more embodiments.

FIG. 4 is a flowchart, of a method 400 for calibrating the SAR measurement, in accordance with one or more embodiments. Method 400 is performed to measure the signal intensity and the power of the MRI system in the unloaded condition. Method 400 may be performed, for example, by MRI system controller 22 and/or MRI data processor 42.

A reference phantom is positioned within the transmit coil before method 400 is performed. The reference phantom may be temporarily or permanently affixed to the coil.

An example reference phantom is a small cylindrical bottle having a length of about 10 cm, diameter of about 3 cm, and filled with oil (e.g., baby oil). The small cylindrical bottle may be temporarily attached to the upper surface of a birdcage coil with tape. Of course, more permanent and robust physical structure for support of the reference phantom(s) is also contemplated. The example, birdcage coil is about 70 cm in diameter, and the small cylindrical bottle is located at about 25 cm above the z-axis (e.g., y=+25 cm) and as far from the patient body as possible but within the field of view (FOV) of the birdcage coil.

At operation 402, the reference phantom image signal in the unloaded $S_{unloaded}$ condition is measured. The measurement is performed using a short scan performed with the reference phantom within the coil. The patient is not located within the coil (e.g. the coil is not loaded) when the calibration is performed. The short scan may utilize a conventional locator pulse sequence such as that shown in FIG. 5.

At operation 404 the peak RF power for the unloaded condition (e.g. when the patient is not loaded into the coil) is determined. The required peak RF power for the unloaded condition is determined based upon the diagnostic scan pulse sequence to be used. According to an embodiment, the system automatically determines the peak RF power based upon the power and timing of RF pulses in the diagnostic sequence selected/set by the operator. Automatic determination of the peak RF power is known in the art when parameters including the diagnostic scan pulse sequence is selected or set.

At operation 406, the measured unloaded reference phantom image signal and the determined required peak RF power for the unloaded condition are stored in a memory for subsequent reference.

Figure 6:
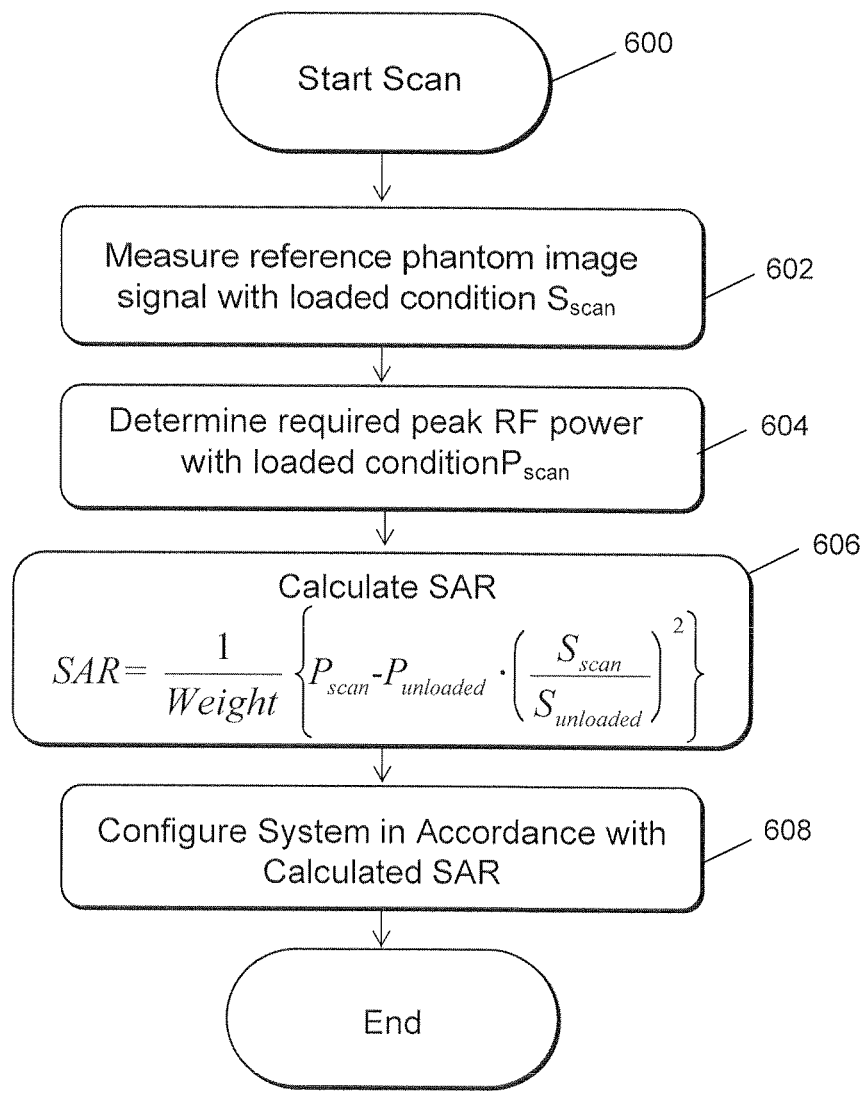
FIG. 6 is a flowchart of a process for determining power and signal parameters when a patient is loaded in a RF coil and to thereby determine SAR using MR signals in accordance with one or more embodiments.

FIG. 6 is a flowchart of a method 600 for determining SAR for a patient, in accordance with one or more embodiments. Method 600 may be performed prior to diagnostic scanning in order to ensure the safety of the patient. Method 600 may be performed by MRI system controller 22 and/or MRI data processor 42. Method 600 is performed with the patient loaded in the RF coil for MRI scanning.

Figure 5:
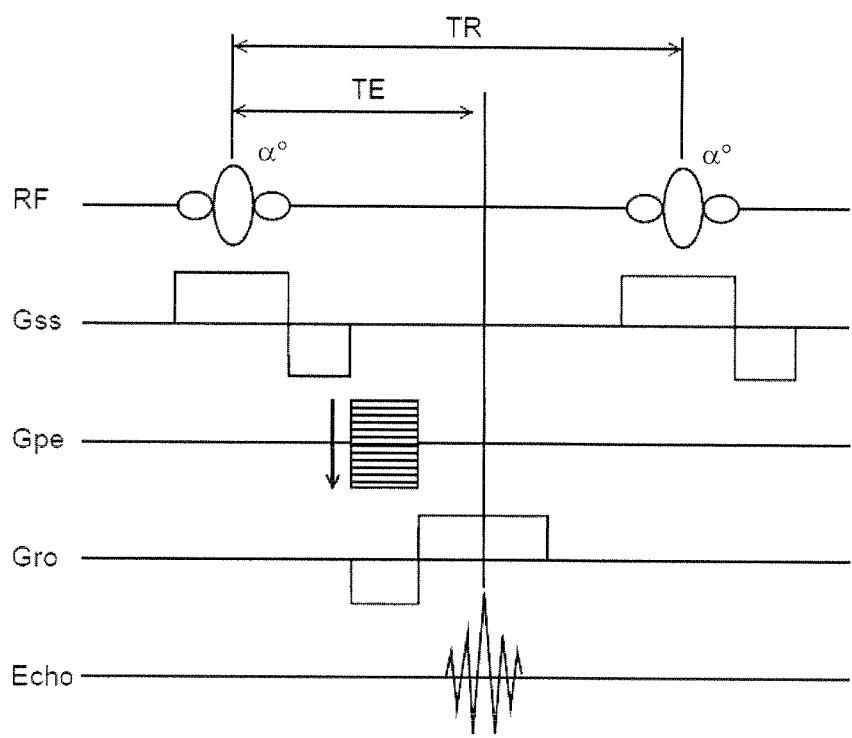
FIG. 5 show an example pulse sequence to determine signal strength at the reference phantom in accordance with one or more embodiments.

After entering the subroutine at 600, at operation 602, in the loaded condition, the reference phantom image signal $S_{scan}$ may be measured using a short locator scan, for example, using the scan sequence shown in FIG. 5.

The short scan may be used as part of a routine clinical imaging protocol. For example, the short scan may be included in a locator scan that is frequently performed in clinical environments as a prescan to determine the exact positioning of the patient. Thus, the short scan may be included in clinical environments without increasing the scan time or requiring additional hardware. The prescan may execute a locator pulse sequence such as that shown in FIG. 5. The pulses of the short locator scan may include frequencies that are off-resonance to water protons, but which excite the reference phantom protons.

At operation 604, the required peak RF power for the selected diagnostic MRI data acquisition scan is determined for the loaded condition. As noted above, the required peak RF power may be automatically determined by the system using known techniques when the diagnostic pulse sequence and the weight of the patient is specified.

At operation 606, the SAR is calculated, for example, based upon Equation 14.

At operation 608, the system and/or the diagnostic scan may be configured in accordance with the calculated SAR. For example, if the calculated SAR exceeds a configured and/or known safety threshold for the patient, then the diagnostic scan may be terminated or reconfigured. Reconfiguration of the diagnostic scan may include the operator, or the system automatically, selecting an alternative diagnostic scan sequence (which can then be re-evaluated for the expected SAR value by repeating operations 602 and 604).

In some embodiments, $P_{coil}$ may be estimated with numerical electromagnetic simulations. Once validated with actual measurements, simulation can provide $P_{coil}$ values for a variety of scan conditions for SAR calculations for a particular MRI system.

In some other embodiments, other sequences (such as "Rapid Radiofrequency Calibration in MRI", by Joe Carlson and Dave Kramer, Magn Reson Med 1990; 15: 438-445) can be applied to directly measure RF flip angle (e.g., for $B_1^+$) in the reference phantom.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) system comprising:
    an MRI gantry including a static magnetic field coil, gradient magnetic field coils, at least one radio frequency (RF) coil configured to transmit RF nuclear excitation pulses into an imaging volume, and to receive nuclear magnetic resonance (NMR) RF signals from a patient located in the imaging volume;
    at least one reference phantom arranged at a location within the at least one RF coil, the location being substantially unaffected by a scattered magnetic field created by the patient; and
    an MRI control system having at least one computer configured to:
        determine a specific absorption rate (SAR) for the patient based on at least (a) NMR signal strength at the phantom when the at least one RF coil is loaded with the patient for an MRI scan, and (b) NMR signal strength at the phantom when the at least one RF coil is not loaded with the patient for an MRI scan.

2. An MRI system as in claim 1, wherein said location is spatially displaced away from the patient towards an end of the at least one RF coil to reduce scattered RF coil field effects.

3. An MRI system as in claim 2, wherein said location is substantially close to a surface of the at least one RF coil.

4. An MRI system as in claim 1, wherein comprising plural reference phantoms arranged at respective different locations within the FOV of the at least one RF coil and wherein said SAR is determined based on relative unloaded and loaded NMR signals from said plural phantoms.

5. An MRI system as in claim 1, wherein said reference phantom is a non-loading object filled with an off water resonance substance.

6. An MRI system as in claim 1, wherein the NMR signal strength at the phantom when the at least one RF coil is loaded with the patient for an MRI scan, and the NMR signal strength at the phantom when the at least one RF coil is not loaded with the patient are determined by applying an NMR pulse sequence with small flip angle pulses.

7. An MRI system as in claim 6, wherein the pulse sequence is a field echo (FE) pulse sequence.

8. An MRI system as in claim 6, wherein the pulse sequence includes pulses at an NMR resonance frequency of the reference phantom which is different from an NMR resonance frequency of water.

9. An MRI system as in claim 1, wherein determining NMR signal strength at the phantom when the at least one RF coil is loaded with the patient for an MRI scan is performed responsive to a locator pulse sequence preceding a diagnostic MRI scan.

10. An MRI system as in claim 1, wherein determining NMR signal strength at the phantom when the at least one RF coil is not loaded with the patient for an MRI scan includes accessing a previously measured and stored value representing the NMR signal strength at the phantom when the at least one RF coil is not loaded.

11. An MRI system as in claim 1, wherein said SAR is calculated using at least: (a) patient weight; (b) NMR signal strength at the phantom when the at least one RF coil is loaded with the patient for an MRI scan; (c) NMR signal strength at the phantom when the at least one RF coil is not loaded with the patient for an MRI scan; and (d) a comparison of power outputs when the at least one RF coil is and is not loaded with the patient for an MRI scan.

12. An MRI system as in claim 1, wherein said SAR is calculated using the following formula:

$$SAR = \frac{1}{\text{weight}}\left\{P_{scan} - P_{unloaded} \cdot \left(\frac{S_{scan}}{S_{unloaded}}\right)^2\right\}$$

where:
weight=patient weight in kilograms;
$P_{scan}$=RF power transmitted to the RF coil when loaded with the patient for an MRI scan;
$P_{unloaded}$=RF power transmitted to the RF coil when not loaded with the patient for an MRI scan;
$S_{scan}$=NMR signal strength at the reference phantom when RF coil is loaded with patient for an MRI scan; and
$S_{unloaded}$=NMR signal strength at the reference phantom when RF coil is not loaded with patient for an MRI scan.

13. An MRI system as in claim 12, wherein calibration values for $P_{unloaded}$ and $S_{unloaded}$ are pre-determined and pre-stored in memory for ready use in calculating SAR during subsequent MRI patient imaging procedures.

14. A magnetic resonance imaging (MRI) method comprising:
configuring and using an MRI system having static and gradient magnetic field generators, at least one radio frequency (RF) coil configured to transmit RF nuclear excitation pulses into an imaging volume, and to receive nuclear magnetic resonance (NMR) RF signals from a patient located in the imaging volume, at least one reference phantom arranged at a location being within the at least one RF coil, the location substantially unaffected by a scattered magnetic field created by the patient, and an MRI control system having at least one configurable computer to:
determine a specific absorption rate (SAR) for the patient based on at least: (a) NMR signal strength at the phantom when the at least one RF coil is loaded with the patient for an MRI scan, and (b) NMR signal strength at the phantom when the at least one RF coil is not loaded with the patient for an MRI scan.

15. The method as in claim 14, wherein said location is spatially displaced away from the patient towards an end of the at least one RF coil to reduce scattered RF coil field effects.

16. The method as in claim 14, wherein the determining NMR signal strength at the phantom without the patient in the imaging volume comprises:
applying an NMR pulse sequence to the imaging volume without the patient; and
measuring NMR signal strength responsive to the pulse sequence at the phantom.

17. The method as in claim 14, determining NMR signal strength at a location with a patient in an imaging volume comprises:
applying an NMR pulse sequence to the imaging volume with the patient being present in the at least one RF coil; and
measuring NMR signal strength responsive to the NMR pulse sequence at the phantom.

18. An MRI method as in claim 14, wherein said SAR is machine calculated using at least: (a) patient weight; (b) NMR signal strength at the phantom when the at least one RF coil is loaded with the patient for an MRI scan; (c) NMR signal strength at the phantom when the at least one RF coil is not loaded with the patient for an MRI scan; and (d) a comparison of power outputs when the at least one RF coil is and is not loaded with the patient for an MRI scan.

19. An MRI method as in claim 14, wherein said SAR is calculated using the following formula:

$$SAR = \frac{1}{\text{weight}}\left\{P_{scan} - P_{unloaded} \cdot \left(\frac{S_{scan}}{S_{unloaded}}\right)^2\right\}$$

where:
weight=patient weight in kilograms;
$P_{scan}$=RF power transmitted to the RF coil when loaded with the patient for an MRI scan;
$P_{unloaded}$=RF power transmitted to the RF coil when not loaded with the patient for an MRI scan;
$S_{scan}$=NMR signal strength at the reference phantom when RF coil is loaded with patient for an MRI scan; and
$S_{unloaded}$=NMR signal strength at the reference phantom when RF coil is not loaded with patient for an MRI scan.

20. A non-transitory computer readable storage medium having instructions stored thereon that, when executed by a computer of an MRI system having static and gradient magnetic field generators, at least one radio frequency (RF) coil configured to transmit RF nuclear excitation pulses into an imaging volume, and to receive nuclear magnetic resonance (NMR) RF signals from a patient located in the imaging volume, at least one reference phantom arranged at a location within the at least one RF coil, the location being substantially unaffected by a scattered magnetic field created by the patient, causes the computer to:
determine a specific absorption rate (SAR) for the patient based on at least: (a) NMR signal strength at the phantom when the at least one RF coil is loaded with the patient for an MRI scan, and (b) NMR signal strength at the phantom when the at least one RF coil is not loaded with the patient for an MRI scan.

* * * * *